(12) United States Patent
Lu et al.

(10) Patent No.: US 6,411,907 B1
(45) Date of Patent: Jun. 25, 2002

(54) ACCURATE TISSUE INJURY ASSESSMENT

(75) Inventors: Taiwei Lu, Petaluma; Robert A. Lieberman, Torrance; Emile Fiesler, Torrance; Allan Wang, Torrance, all of CA (US)

(73) Assignee: Intelligent Optical Systems, Inc., Torrance, CA (US)

( * ) Notice: Subject to any disclaimer, the term of this patent is extended or adjusted under 35 U.S.C. 154(b) by 0 days.

(21) Appl. No.: 09/342,303

(22) Filed: Jun. 29, 1999

Related U.S. Application Data

(63) Continuation-in-part of application No. 08/900,319, filed on Jul. 25, 1997.

(51) Int. Cl.[7] ............................................. G01B 15/02
(52) U.S. Cl. ........................................ 702/28; 702/172
(58) Field of Search .................. 702/28, 172; 128/654, 128/664, 665

(56) References Cited

U.S. PATENT DOCUMENTS

| 4,170,987 A | * | 10/1979 | Anselmo et al. ............. 128/665 |
| 4,693,255 A | * | 9/1987 | Beall .......................... 128/654 |
| 5,701,902 A | * | 12/1997 | Vari et al. .................... 128/664 |
| 6,058,352 A | * | 5/2000 | Lu et al. ....................... 702/28 |

* cited by examiner

*Primary Examiner*—John S. Hilten
*Assistant Examiner*—Douglas N Washburn
(74) *Attorney, Agent, or Firm*—Nilles & Nilles, S.C.

(57) ABSTRACT

Systems and methods using a spectrometer system for real-time automatic evaluation of tissue injury are described. A method of assessing an injury to tissue comprises reflecting an electromagnetic signal from the tissue to produce a reflected electromagnetic signal; producing spectral data pertaining to the intensities of individual wavelengths of the reflected electromagnetic signal; analyzing the spectral data to obtain a set of results; and providing an indication of the nature of the injury to the tissue based upon the set of results.

15 Claims, 3 Drawing Sheets

ACCURATE TISSUE INJURY ASSESSMENT

This application is a continuation-in-part of application Ser. No. 08/900,319, filed Jul. 25, 1997, entitled "Accurate Tissue Injury Assessment Using Hybrid Neural Network Analysis."

BACKGROUND OF THE INVENTION

1. Field of the Invention

The present invention relates generally to the field of tissue injury analysis. More particularly, the present invention relates to a method and apparatus for objective tissue injury analysis. Specifically, a preferred embodiment of the invention relates to a method in which spectral data is produced that pertains to the intensities of individual wavelengths of an electromagnetic signal reflected from the tissue injury, and then an indication of the nature of the injury to the tissue is provided based upon the results of analyzing the spectral data. The present invention thus relates to a method and apparatus for tissue injury analysis of the type that can be termed objective.

2. Discussion of the Related Art

Within this application several publications are referenced. The disclosures of all these publications in their entireties are hereby expressly incorporated by reference into the present application for the purposes of indicating the background of the present invention and illustrating the state-of-the-art.

Tissue injury is common in daily life. Tissue injuries include, for example, burns, rashes, skin infections (inflammations), and allergic reactions associated with allergies and tests for allergies. With respect to burn injuries in particular, for example, approximately 70,000 serious burn cases are reported in the United States every year, at a cost to the economy of an estimated two billion dollars. Traditionally, burns have been classified as first, second, or third degree, based on visual criteria. First-degree burns are visually indicated by redness and blistering of the skin. Second-degree burns are visually indicated by withering of the skin without charring. Third-degree burns are visually indicated by eschar formation and charring.

This type of classification, which has been used with only minor alterations for nearly two hundred years, is concerned chiefly with the intensity of burning and not with the depth of tissue destroyed. Only recently have burn physicians come to realize that the depth of injury is of greater importance than superficial appearance. The classification of burns that has recently been adopted has completely forsaken all reference to outward appearances, which are only an indication of the severity of surface burning. The new type of classification recognizes two degrees of burn injury. The first new classification is partial-thickness skin loss, implying the presence of sufficient living epithelial elements to resurface the area. The second new classification is full-thickness skin loss, implying virtually complete destruction of all epithelial elements so that healing can only occur by contraction of the wound and epithelial cell migration from the edge of the wound or by surgical intervention.

Proper treatment depends on the correct classification of the burn. Further, early differentiation between these two degrees of burns is critical for several reasons. It is better to excise dead tissue and close the wound than to allow spontaneous separation of the slough, with its attendant risks of infection, fibrosis, and loss of function. Surgical results are best when the proper treatment is taken within the shortest time. The sooner a definite diagnosis is made, the sooner the patient can leave the hospital, decreasing costs for both the hospital and the patient. In life-threatening burns, and especially when donor sites are at a premium, it is very important to distinguish quickly between full-thickness and partial-thickness burn injuries.

Figure 1:
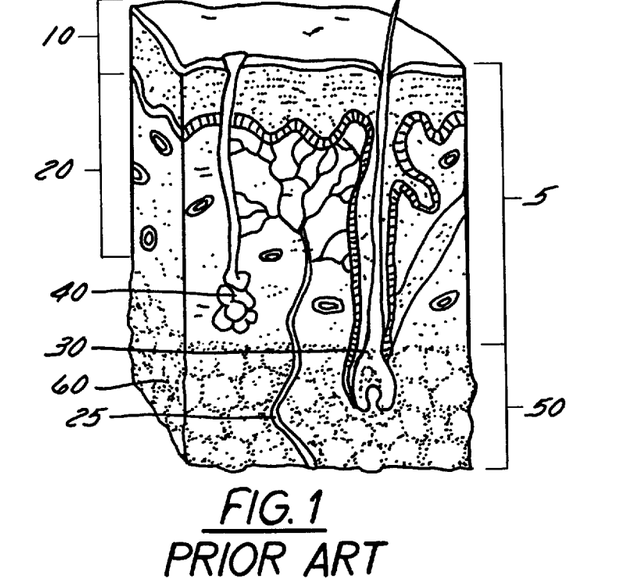
FIG. 1 illustrates an isometric sectional view of human skin, appropriately labeled "prior art"

FIG. 1 shows a model of a three dimensional section of human skin. Two major tissue layers are conventionally recognized as constituting human skin 5. The outer layer is a thin stratified epithelium, called the epidermis 10, which varies relatively little in thickness over most of the body. The human epidermis is typically between 75 $\mu$m and 150 $\mu$m thick. Underlying the epidermis 10 is a dense layer of fibrous elastic connective tissue, called the dermis 20, which constitutes the mass of skin. The dermis 20 supports extensive vascular and nerve networks, and encloses specialized excretory and secretory glands and keratinized appendage structures such as hair and nail. Beneath the skin is the subcutaneous tissue, or hypodermis 50, which is variously composed of loose areolar connective tissue or fatty connective tissue displaying substantial regional variations in thickness. Nerves 25 pass through the hypodermis 50. Of particular interest is the presence and depth of hair follicles 30 and sweat glands 40 in the dermis. The bases of these structures are surrounded by cells capable of forming new "skin." These cells lie very close to the interface of the dermis and the subcutaneous fat 60, and represent the vital plane insofar as spontaneous skin repair is concerned. If destruction occurs below this vital plane, the burn is a full-thickness burn; if above this vital plane, it is a partial-thickness burn.

The blood supply in the skin comes from cutaneous branches of the subcutaneous musculocutaneous arteries. Branches arising from the cutaneous arteries give rise to a distinctive small vessel plexus which lies deep in the dermis near and parallel to the interface with the subcutaneous tissue. Therefore, destruction of a large area of hair follicles and sweat glands in a full-thickness burn devascularizes the skin in the same area. This is the basis of several previous burn diagnosis methods that use the new type of classification.

However, classifying a burn is not easy immediately after the burn occurs, and usually depends upon intuition about the appearance of the burn rather than upon accurate description and definition (i.e., objective characterization). Early visual assessment may be difficult because the ability of the wound to heal depends strongly on the condition of underlying tissues, which in the case of severe burns are generally obscured by overlying layers of dead and denatured skin. Thus, three days after burns were incurred, the surgeons in one study were only willing to commit themselves to a predication in about two thirds of the cases. Heimbach, D. M., Afromowitz, M. A., Engrav, L. H., Marvin, J. A. and Perry, B., "Burn Depth Estimation—Man or Machine," *The Journal of Trauma*, vol. 24, No. 5, pp. 373–378 (1984). One fourth of the predictions made at this time were incorrect. In an effort to address this problem many objective diagnostic methods have been proposed by previous researchers. These methods take information from the surface, as well as beneath the skin, and depend on the following criteria and procedures. One method depends on a fluorescein test for the presence of dermal circulation. Another method depends on staining reactions on the surface of the burn. Another method depends on sensitivity of the burn to pinprick. Yet another method depends on temperature variations within the burn area as evidenced by thermogram.

Although some progress has been made in laboratory testing, heretofore, no method has gained widespread clinical acceptance. The limitations of previous methods include poor burn depth predictive values on various selected days post-burn, excessive cost, cumbersome techniques, time-consuming techniques, and techniques that often include a toxic reaction.

These previous methods can be classified either as invasive or non-invasive. The invasive methods include the fluorescence test, staining appearance, and sensitivity to pinprick. The non-invasive approaches are the thermogram imaging and multispectral photographic analysis.

The fluorescence method employs a fluorometer to quantify fluorescence as a measure of burn depth. However, the fluorescein injected into the femoral vein in this method causes a toxic reaction in some patients. Green, H. A., Bua, D., Anderson, R. R. and Nishioka, N. S., "Burn Depth Estimation Using Indocyanine Green Fluorescence." *Arch Dermatol*, vol. 128, January, pp. 43–49 (1992).

The staining reaction method introduced by Patey and Scarff maps out areas of surface necrosis using dyes such as hematoxylin, marking the absence of blood circulation. Patey, D. H. and Scarff, R. W., *British Journal of Surgeon*, vol. 32, pp. 32 (1944). However, this method reveals nothing about skin layers deeper than the eye can see, whereas the critical layer in burns under the new type of classification is the deepest plane of living epithelial elements.

While the pinprick method is self-explanatory, it is often inaccurate in predicting the depth of a burn. In addition, this method can result in significant blood loss. Jackson, D. M., "In Search of an Acceptable Burn Classification." *British Journal of Plastic Surgeon*, vol. 23, pp. 118–145 (1970).

Thermography, the measurement of the infrared waves emitted by all objects, is time consuming in that it usually requires at least 20 minutes in an air-conditioned room. Mladick, R., Georgiade, N. and Thorne, F., "A Clinical Evaluation of the Use of Thermography in Determining Degree of Burn Injury." *Plastic and Reconstructive Surgery*, Vol. 38, No. 6, pp. 512–518 (1966). Further, thermography devices are very costly.

Anselmo and Zawacki developed a method based on rationing the magnitudes of visible and infrared radiation from several spectral ranges. Anselmo, V. J. and Zawacki, B. E., "Multispectral Photographic Analysis: A New Quantitative Tool to Assist in the Early Diagnosis of Thermal Burn Depth." *Annals of Biomedical Engineering*, Vol. 5, pp. 179–193 (1977). Although their results were promising, the analysis time was too slow for clinical decision making.

Heimbach developed a burn depth estimation approach called the Burn Depth Indicator (BDI) method. Heimbach, D. M., Afromowitz, M. A., Engrav, L. H., Marvin, J. A. and Perry, B., "Burn Depth Estimation—Man or Machine," *The Journal of Trauma*, vol. 24, No. 5, pp. 373—378 (1984). It is similar to the method of Anselmo and Zawacki (relating burn depth to the ratios of red/green, red/infrared, and green/infrared light reflected from the burn wound), but is much faster. This approach is based on the premise that the reflectance intensity of different optical wavelength ranges corresponds to different degrees of burns, and more specifically on the premise that green and red light are important for partial-thickness burns and red and infrared are important for full-thickness burns. Heimbach's experimental results show that the BDI method is significantly more accurate than clinical assessment in cases where surgeons subjectively predicted burn injuries would not heal. The BDI method is reported to have maintained an accuracy of 79% for wounds for which the surgeons would not make a prediction.

However, limited data analysis techniques allowed Heimbach to choose only the average intensity in each of several specific frequency ranges. This may have restricted the prediction accuracy and the application of the BDI method because the details of these frequency ranges may be different for different degrees of burn even though their averages are nearly the same. Further, other frequency ranges may also contain information about the classification of a burn injury.

Other tissue injuries for which better assessment accuracy is needed include contusions, bedsores, and skin cancer. Other areas in which improved assessment accuracy is needed include monitoring skin for signs of skin cancer and characterizing biological tissues in general for blood perfusion, oxygenation, and arterial blood gas levels.

SUMMARY AND OBJECTS OF THE INVENTION

A primary object of the invention is to provide an apparatus that accurately classifies tissue injuries. Another object of the invention is to provide an apparatus that is cost effective. It is another object of the invention to provide an apparatus that is rugged and reliable, thereby decreasing down time and operating costs. It is yet another object of the invention to provide an apparatus that has one or more of the characteristics discussed above but which is relatively simple to manufacture and assemble using a minimum of equipment.

In accordance with a first aspect of the invention, these objects are achieved by providing an apparatus for assessing an injury to a tissue, comprising an electromagnetic signal generator; an optical fiber connected to the electromagnetic signal generator; a fiber optic probe connected to the optical fiber; a broad band spectrometer connected to the fiber optic probe; and a computer connected to the broad band spectrometer. The computer analyzes data from the broad band spectrometer to produce a plurality of outputs each of which corresponds to a tissue injury category. The computer includes a principle component analyzer of broad band spectral data obtained from the broad band spectrometer. The computer produces a set of results at the plurality of outputs which indicate the nature of the injury to the tissue.

It is another object of the invention to provide a method that is predictable and reproducible, thereby decreasing variance and operating costs. It is yet another object of the invention to provide a method that has one or more of the characteristics discussed above but which is relatively simple to setup and operate using moderately skilled workers.

In accordance with a second aspect of the invention, these objects are achieved by providing a method of assessing an injury to tissue comprising reflecting an electromagnetic signal from the tissue to produce a reflected electromagnetic signal; producing spectral data pertaining to the intensities of individual wavelengths of the reflected electromagnetic signal; analyzing the spectral data to obtain a set of results; and providing an indication of the nature of the injury to the tissue based upon the set of results.

These, and other, aspects and objects of the present invention will be better appreciated and understood when considered in conjunction with the following description and the accompanying drawings. It should be understood, however, that the following description, while indicating preferred embodiments of the present invention and numerous specific details thereof, is given by way of illustration and not of limitation. Many changes and modifications may be made within the scope of the present invention without departing from the spirit thereof, and the invention includes all such modifications.

BRIEF DESCRIPTION OF THE DRAWINGS

A clear conception of the advantages and features constituting the present invention, and of the construction and operation of typical mechanisms provided with the present invention, will become more readily apparent by referring to the exemplary, and therefore nonlimiting, embodiments illustrated in the drawings accompanying and forming a part of this specification, wherein like reference numerals designate the same elements in the several views, and in which.

DESCRIPTION OF PREFERRED EMBODIMENTS

The present invention and the various features and advantageous details thereof are explained more fully with reference to the nonlimiting embodiments that are illustrated in the accompanying drawings and detailed in the following description. Descriptions of well-known components and processing techniques are omitted so as to not unnecessarily obscure the present invention in detail.

To describe the invention with regard to a specific embodiment, the following discussion addresses many aspects of a system that is optimized for burn analysis without in any way limiting the invention to specific injuries, or corresponding spectral wavelengths.

Figure 2:
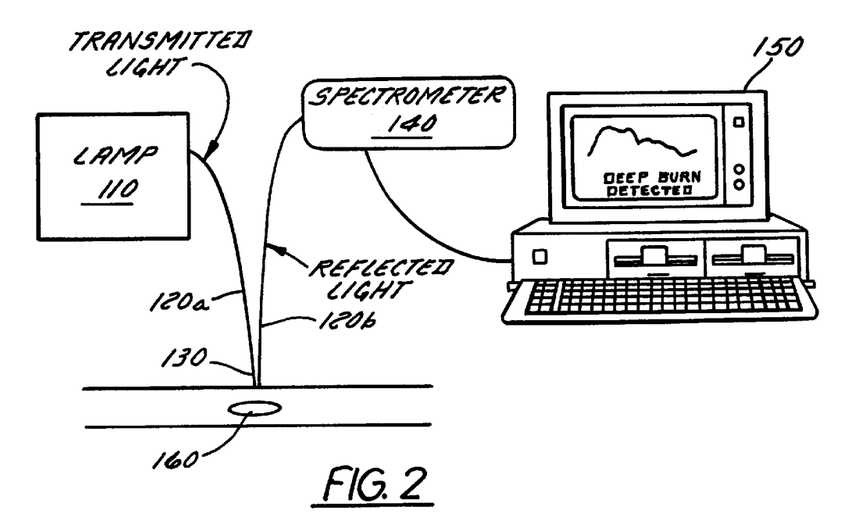
FIG. 2 illustrates a schematic view of a portable tissue injury analyzer system according to the present invention.

Referring now to FIG. 2, a spectroscopic burn analysis system is shown. The system includes a tungsten halogen lamp 110 (a broad band UV, visible, and near infrared light source), optical fibers 120a and 120b, an optical probe 130, a fiber optic spectrometer 140 and data acquisition and hybrid neural network or static analysis software running on a personal computer 150.

Figure 3:
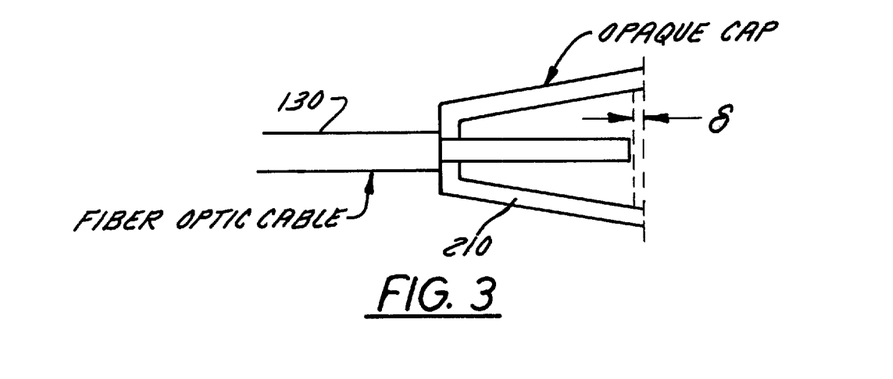
FIG. 3 illustrates a sectional view of a probe according to the present invention.

In operation, optical probe 130 is positioned against burned skin 160. Light from the lamp 110 is transmitted through the optical fiber 120a, exits the optical probe 130, and is reflected from the burn site. The center of the probe 130 can be designed so that it receives reflected light and the surrounding area delivers the source light. A cut-away side-view of the probe 130 is illustrated in FIG. 3, where δ is the distance between the tip of the optical probe 130 and the end of the optical fiber. As shown therein, an opaque cap 210 can advantageously prevent light from other sources from entering the probe. Similarly, it can be advantageous to locate the patient within a dark enclosure so that it is not necessary to touch the tissue.

Light is reflected and collected from the burn site only as long as is required to acquire data samples across the entire spectrum (about one second or less). The optical probe 130 is held fixed while the data samples are acquired.

The light reflected from the burn site is returned through the optical fiber 120b to the fiber optic spectrometer 140. In the embodiment of FIG. 2, the fiber optic spectrometer 140 comprises a single photodetector. The photodetector should have as high a resolution as is practical in terms of its ability to distinguish light at different wavelengths. If it is desired to obtain measurements from different locations on the burn site, then the optical probe 130 may be repositioned at the different locations along the burn site and more data collected. Alternatively, an array of photodetectors could also be used.

The spectrometer 140 performs a spectral analysis of the light reflected from the burn site. In the illustrated embodiment, each acquired spectrum contains 1100 samples covering wavelengths from 550 nm to 1030 nm. The data is stored in the form of a one-dimensional array ($x_1 \ldots x_{1100}$), where each of the different values of $x_i$ corresponds to the intensity of a different individual wavelength within the spectrum 550 nm to 1030 nm. Because 1100 samples are obtained covering wavelengths from 550 nm to 1030 nm, each individual wavelength, as the term is used herein, is actually a narrow band of wavelengths. In the embodiment described herein, the narrow band of wavelengths is approximately 0.435 nm in width. If desirable, the raw spectral data may be displayed using the personal computer 150 in the form of a graph of spectral intensity as a function of wavelength.

Intelligent analysis and interface software based on the hybrid neural network can be used to operate a low-cost spectrometer and an optimized fiber probe. Thus, general hospitals and emergency units can afford an accurate and reliable system for objective tissue injury classification.

The system shown in FIG. 2 includes a system that automatically classifies tissue injuries such as, for example, partial-thickness and full-thickness skin loss due to burns, by analyzing multiple wavelengths in the visible and near-infrared ranges (i.e., from 500 nm to 1030 nm). The invention can also analyze wavelengths in the UV range.

Figure 4:
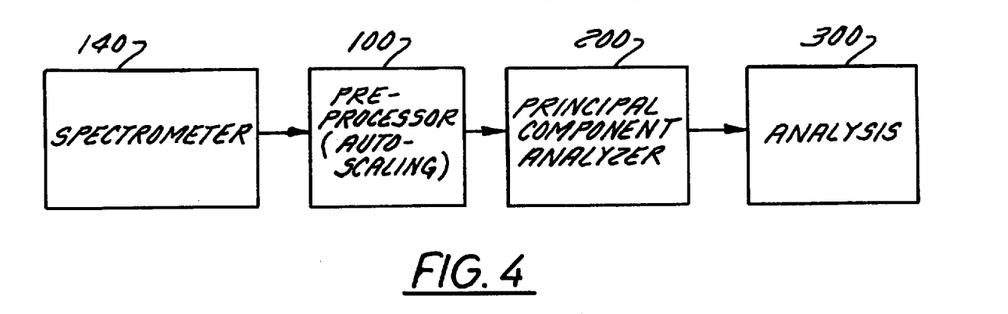
FIG. 4 illustrates a block diagram view of a flow of spectral signal processing according to the present invention.

Referring to FIG. 4, the spectrometer 140 that can include UV, visible and near infrared (IR) capabilities is combined with a hybrid neural network for tissue injury spectral analysis that involves three procedures; preprocessing 100 (autoscaling), principal component analysis 200, and back-propagation neural network processing 300. Each procedure is explained in detail in this section.

Preprocessing

Once a broad band spectrum is provided by a broad band spectrometer, it is preprocessed by autoscaling, because the amplitudes of the data sets vary according to the adjustment of the acquisition instrument and the distance and angle between the sensor and the tissue wound area. The absolute values of the intensities of individual wavelengths are not significant. The mean and variance of each spectrum (i.e., the mean wavelength intensity and the variance of the wavelength intensities) can be calculated as follows:

$$\bar{x} = \frac{1}{N} \sum_{i=0}^{N-1} x_i \tag{1}$$

$$\sigma^2 = \frac{1}{N-1} \sum_{i=0}^{N-1} (x_i - \bar{x})^2 \qquad (2)$$

where $\bar{x}$ is the mean wavelength intensity, $\sigma^2$ is the variance of the wavelength intensities, $x_i$ is an input datum (i.e., the intensity of a particular wavelength in the spectrum) and N is the number of samples in that spectrum. After autoscaling, the output data $s_i$ can be computed as follows:

$$s_i = \frac{x_i - \bar{x}}{\sqrt{\sigma^2}} \qquad (3)$$

After autoscaling, the output for every spectrum has a zero mean and unit variance.

Principal Component Analysis (PCA)

PCA (K-L transform) is widely used in signal and image processing for data compression and feature extraction. Especially in the field of analytical chemistry, PCA is commonly employed to distinguish different chemical compounds within a single spectrum. When the number of data sets is large, PCA is very effective for dimension reduction. There are two main reasons for using PCA to deal with tissue injury spectra. First, the acquired spectrum of each tissue injury can include a large number of data points, for example one to ten thousand data points. In the present example, in which 1100 samples are collected, there are 1100 data points (i.e., $x_1, \ldots, x_{1100}$ or, assuming the autoscaled data points are utilized, $s_1, \ldots, s_{1100}$). Most of these data points are redundant and, in any event, it is not practical to use all of this data in the neural networks for pattern recognition. Second, screening spectra for such tissue injuries as, for example, full-thickness and partial-thickness burn injuries, typically reveals no obvious peaks that can be used for characterization (e.g., depth of burn). Therefore, it is very difficult to extract information from any specific frequency range to distinguish between different characterizations.

PCA involves transforming a block of data in one representation to another representation in which a large fraction of its total energy is contained in relatively few transform coefficients. The representation dimensions ("bases") are all orthogonal after transformation. They are called "eigenspectra." Each input spectrum can be projected onto these orthogonal bases and its corresponding coefficients can be calculated to represent the spectrum in the transformed domain. Of several methods that can be used to implement PCA, the method of singular value decomposition (SVD) is well suited to find the principal components of the data set for the purpose of implementing the present invention.

Singular value decomposition is based on a theorem of linear algebra. This theorem that states any matrix A of M×N (i.e., M rows by N columns), with M>N, can be written as a product of an M×N column orthonormal matrix U, and an M×N diagonal matrix W with non-negative elements, and the transpose of an N×N orthonormal matrix V, i.e., $$A = U W V^T, \qquad (4)$$

where the superscript T represents the transposition of a matrix and the matrix A is the spectrum data matrix. More specifically, in the present embodiment, the matrix A is a single column matrix (N=1) with 1100 rows formed by the data points $s_1, \ldots, s_{1100}$ (M=1100).

The column vectors of $V^T$, or the row vectors of V, can be regarded as the orthonormal bases of an N-dimensional vector space. In view of Equation (4), the matrix $$B = A V = U W \qquad (4a)$$

then represents the projection of A onto $V^T$ (V), with the projection strength on the I-th base given by the I-th element $w_{ii}$ of W. Small projections of A on some vector bases of $V^T$ can be ignored because they are dominated by noise or round-off error in the data matrix A. The small projections can be removed by setting one or many smallest elements of W to zero. This procedure creates a trimmed version of W, which will be referred to as $W_1$. The matrix $$B_1 = U W_1 \qquad (5)$$

then preserves all major projections of A onto $V^T$; therefore, the data points of the column vector $B_1$ are called the principal components of the original matrix A. Upon performing the PCA, the original data matrix A is transformed to a lower-dimensional matrix $B_1$, with noise and error removed to a certain level. For example, the matrix $B_1$ may be a single column matrix with 12 rows of data points.

After PCA, the spectral data is represented by fewer coefficients. However, the fact that these coefficients have different scales can reduce the speed of the subsequent neural network training. Another autoscaling step is preferably applied to these coefficients, making the neural network training much faster.

Neural Network Processing

Figure 5A:
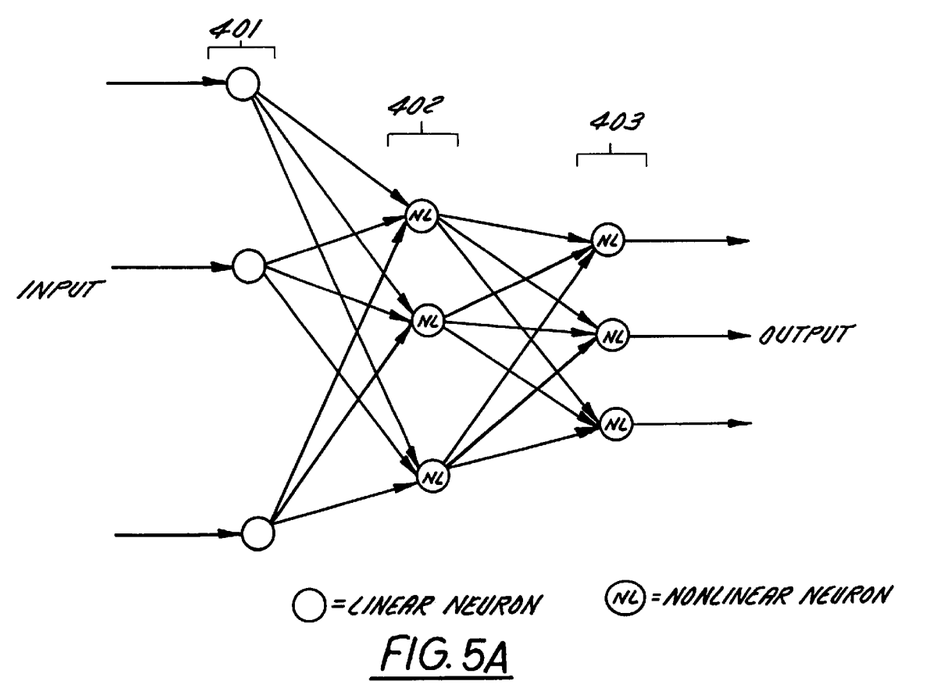
FIG. 5A illustrates a schematic diagram view of a multilayer neural network structure according to the present invention.

Artificial neural networks are very popular in, for example, pattern recognition, control engineering, and communication.[8-13] FIG. 5A shows the structure of a multilayer neural network (MLNN). Because of their simplicity, MLNNs are in common use in pattern recognition applications.

Inputs to the network are passed to the neurons in the first layer 401. These inputs will be designated $s_1, \ldots, s_n$. As previously noted, in the preferred embodiment, the spectral data from the spectrometer 140 is autoscaled, processed by way of principal component analysis, and then autoscaled again. Therefore, in the preferred embodiment, the input data points $s_1, \ldots, S_n$ are the outputs of the second autoscaling operation. However, as also previously noted, the autoscaling steps and the principal component analysis are optional. Therefore, it should be understood that the input data $s_1, \ldots, S_n$ could instead correspond to the original sampled data points. Also, other schemes for preprocessing the raw spectral data from the spectrometer 140 are possible and, in this case, the input data $s_1, \ldots, s_n$ would be the output of whatever preprocessing scheme is used.

The outputs of the first layer neurons become inputs to the second layer 402, and so on. The outputs of the network are therefore the outputs of the neurons in the final layer 403. All the neurons in a layer are normally fully connected to the neurons in adjacent layers (interlayer connections), but there is normally no connection among neurons within a layer (intralayer connections) and normally no connection bridging layers (supralayer connections) 10. The input-output relationship between any two connected neurons is determined by the connection weight $W_i$, a bias parameter, and a nonlinear activation function $f(\ )$, as follows:

$$y = f(\Sigma W_i s_i + \theta), \qquad (6)$$

where $s_i$ are the neuron inputs and y is the neuron output. The activation function $f(\ )$ for each hidden and output neuron can be a sigmoid function such as:

$$y = f(u) = \frac{1}{1+e^{-u}} \quad (7)$$

where u is the neuron input $$u = \Sigma W_i s_i + \theta \quad (8)$$

The activation for each input neuron is typically chosen to be linear.

The neural network learns from training samples to associate output characteristics with potentially complex combinations of features in the input. Adaptive learning, massive interconnection, and nonlinear classification capabilities make neural networks generally very robust to noise and distortion, and more sensitive for signal identification and classification than conventional methods. A MLNN is a good choice to perform nonlinear transformation and to recognize spectra of different classes of tissue injuries. The inputs to the neural network are the coefficients of the PCA output. The outputs from the neural network correspond to tissue injury categories, such as, for example, burn classifications.

Static Mathematical Analysis

Figure 5B:
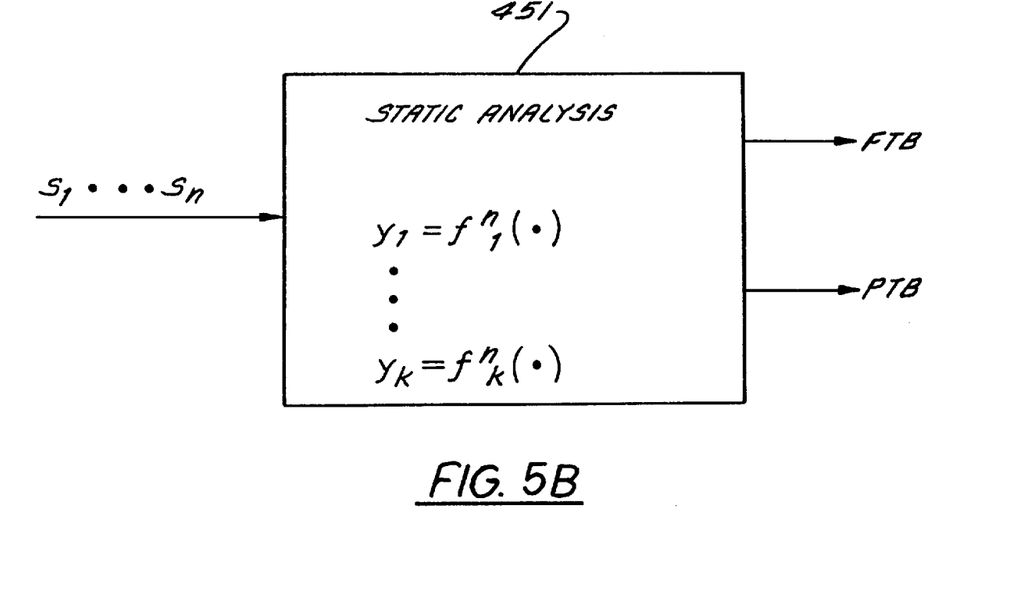
FIG. 5B illustrates a block diagram of an analysis utilized according to the present invention.

As an alternative to the neural network processing described in the previous section, it is also possible to analyze the output of the principal component analysis using static mathematical processing. Such an arrangement is shown in FIG. 5B.

In this arrangement, the coefficients from the principal component analysis are presented to a system of functions 451 operating on polynomials. A general example of such a system of functions is as follows:

$$\begin{cases} y_1 = f_1^2 \left[ \sum_j c_{j1}^2 f_1^1 \left[ \sum_i c_{ij}^1 s_i \right] \right] \\ \vdots \\ y_k = f_k^2 \left[ \sum_j c_{jk}^2 f_k^1 \left[ \sum_i c_{ij}^1 s_i \right] \right] \end{cases} \quad (9)$$

were the functions $f_k^n$ are single-valued functions, and $c_{ij}^n$ and $C_{jk}^n$ (that is, $c_{ij}^1$ and $C_{jk}^2$ in equation (9)) are coefficients from a matrix, and $y_1 \ldots y_k$ are the outputs of the static analysis and are proportional to the probability that the signal is of class k. Any of the variables and coefficients could have a value of zero.

The system of functions 451 comprises k functions, where k corresponds to the number of possible outputs or classes. For example, k is equal to three in the case where there are three possible outputs (e.g., full-thickness burn, partial-thickness burn, no burn). In the example given, the functions have a nesting order (n) of two. The functions could also have a higher nesting order or could be unnested. Each of the functions $f_k^n$ can be different from each other, each can be nonlinear or linear (including the identity function) and each can have shared variables with the other functions.

The functions are a mathematical description of the final (static) state of a neural network (i.e., once the weighting coefficients are determined). Likewise, the coefficient matrices that contain the coefficients $c_{ij}^1$ and $c_{jk}^2$ may be determined mathematically, in principle, in the same manner that the weighting coefficients for a neural network are determined. Like a neural network-based system, the coefficients are determined in advance, before the tissue analysis system is sold, and then simply stored in the computer 150.

The values $y_1 \ldots y_k$ are the outputs of the static analysis and are proportional to the probability that the signal is of class k. Thus, if there are three classes, $y_1$ is proportional to probability that the signal is of class 1 (e.g., full-thickness burn), $y_2$ is proportional to probability that the signal is of class 2 (e.g., partial-thickness burn), and $y_3$ is proportional to probability that the signal is of class 3 (e.g., no burn).

Additionally, a further level of outputs of the analysis could be generated by adding a further outer nested function that is defined as a threshold-type step function. Thus, each of the functions would yield a value of 1 if a threshold probability was exceeded by the next inner level of the nested functions, and would yield a value of 0 if the threshold probability was not exceeded. Thus, the analysis system would then simply indicate that there is a full-thickness bum, partial-thickness burn, or no burn, without indicating the probability associated with each.

A simplified example of such a series of equations is as follows. In the following example, the spectral data consists of three data points, and two possible outputs for the system are assumed: "full-thickness burn" (FTB) and "partial-thickness burn" (PTB). Therefore, there are two classes (k=2). For simplicity, a singular set of nonlinear functions is used instead of nested functions, and so the nesting order is equal to one (n=1). The following coefficient matrix is assumed:

$$c_{ij}^1 = \begin{pmatrix} 0.2 & 3.0 \\ 9.0 & 1.1 \\ 0.2 & 5.0 \end{pmatrix}$$

The coefficient matrix has two columns corresponding to the two outputs (k=2), and three rows corresponding to the input vector length. In practice, of course, the coefficient matrix would typically be much larger since more than three data points would be used. The following system of two nonlinear functions, which share variables with each other, is utilized:

$$\begin{cases} x_1 = f_1^1(c_{11}^1 \cdot s_1 + c_{12}^1 \cdot s_2 + c_{13}^1 \cdot s_3) \\ x_2 = f_2^1(c_{21} \cdot s_1 + c_{22}^1 \cdot s_2 + c_{23}^1 \cdot s_3) \end{cases}$$

The first nonlinear function $f_1$ (corresponding to FTB) is a step function which yields 1 when its input is greater than 6.0 and which yields 0 otherwise. The second non-linear function $f_2$ (corresponding to PTB) is a similar step function which yields 1 when its input is greater than 3.0 and which yields 0 otherwise.

It should also be noted that, in addition to the hybrid neural network analysis embodiment and the static mathematical analysis embodiments that have been described, other embodiments are also possible that use other types of analysis.

EXAMPLE

A more specific embodiment of the present invention will now be described by the following, nonlimiting example which will serve to illustrate various features of significance. The example is intended merely to facilitate an understanding of ways in which the present invention may be practiced and to further enable those of skill in the art to practice the present invention. Accordingly, the example should not be construed as limiting the scope of the present invention.

To prove the feasibility of the present approach, the capability to distinguish between data collected from two types of burns has been clinically demonstrated. The data was collected at the Seattle Burn Center. One set of data represented superficial skin loss and the other set of data represented full-thickness skin loss. A hybrid neural network (HNN) including a preprocessing algorithm (principal components analysis (PCA)), and a multi-layer neural network was used to classify these data sets. The experiment showed 90% accuracy for the examination of 112 samples.

In more detail, a compact spectrometer was used to collect data covering the wavelengths from 500 nm to 1030 nm. A total of 112 samples (spectra) were collected representing 74 cases of superficial and 38 cases of full-thickness skin loss. The data sets were first sorted into two groups. The first group of 56 samples were used for neural network training, and the other 56 samples for testing. Autoscaling was applied to each spectrum so that it has zero mean and unit variance. Then the PCA was employed to produce 10 coefficients from about 1100 data points in each spectrum. The largest ten components were chosen as orthogonal dimension bases. Thus, only ten coefficients remained after PCA instead of 1100 data points in each spectrum. Finally, a MLNN with ten input units, four hidden units, and two output units was trained for about 1500 cycles, producing 51 correct identifications and 5 incorrect responses with the training data set, and 49 correct and 7 incorrect with the testing data set. Thus, the percentage of correct identifications is approximately 90%. Detailed results are shown in Tables I and II. The training time on a 33 MHz personal computer that implements the MLNN in software was approximately 5 minutes.

TABLE I

Results of Training Data Set Classification

| Severity of Burn | Number of Data Sets | Number Correctly Classified | Accuracy |
| --- | --- | --- | --- |
| Superficial | 37 | 36 | 97.3% |
| Full-Thickness | 19 | 15 | 78.9% |
| Total | 56 | 51 | 91.1% |

TABLE II

Results of Testing Data Set Classification

| Severity of Burn | Number of Data Sets | Correct Recognition | Accuracy |
| --- | --- | --- | --- |
| Superficial | 37 | 34 | 91.9% |
| Full-Thickness | 19 | 15 | 78.9% |
| Total | 56 | 49 | 87.5% |

Thus, preliminary clinic results using this neural network based instrument unexpectedly showed approximately 90% accuracy in classifying superficial versus deep burn wounds in patients in a Burn Center. This is a significant improvement over both experienced doctors (whose accuracy is around 50%) and the BDI method (whose accuracy is around 75%).

This example successfully completed a feasibility study of a neural-network-based burn analyzer that is an embodiment of the invention. In this embodiment, a low-cost visible and near infrared (IR) spectrometer was used with a fiber probe to take spectral signals from actual burn patients. An advanced signal processing algorithm was developed to process the data and classify the burns into two categories in real-time.

Needless to say, a practical application of the present invention which has value within the technological arts is objective analysis of wounds such as tissue injuries (e.g., burn injuries). Further, all the disclosed embodiments of the present invention are useful in conjunction with diagnostic techniques such as are used for the purpose of monitoring patients for contusions, bed sores, subdural hematoma, signs of skin cancer, or for the purpose of characterizing biological tissues, blood perfusion, oxygenation and arterial blood gas levels, or the like. The present invention can also be used to detect fluorescent markers. The present invention can also be used in industrial process control and environmental monitoring. There are virtually innumerable uses for the present invention described herein, all of which need not be detailed here. The present invention also can be applied to the following applications of diagnosis, monitoring skin or mucous membrane associated diseases, and monitoring the changes of skin color and pattern during the courses of therapy:

First, the present invention may be used for diagnosing and monitoring all rashes developed on skin and mucous membranes. A rash is any eruption, lesion, or roseola of the skin. Rashes are often associated with communicable infectious diseases, and are usually a shade of red, which varies with the disease. Assessment of the rash includes location and characteristics, such as size (diameter and height), pattern (discrete or coalesced), and any secondary changes (crusting, lichenification, or scaling). The present invention may be used for diagnosing, and monitoring many types of skin and mucous rashes including, but not limited to: Angioedema, nettle rash, or urticaria (hives), butterfly rash or discoid lupus erythematosus, diaper rash or diaper dermatitis, drug rash or dermatitis medicamentosa, ecchymotic rash or hemorrhagic rash, gum rash, tooth rash, or red rash, heat rash, prickly heat, or miliaria (sudamina, rubra, and profunda), hemorrhagic rash or macular rash, maculopapular rash, mercurial rash, mulberry rash, rose rash, serum rash or serum sickness, sunburn like rash or toxic shock syndrome, wandering rash or geographic tongue.

Second, the present invention may also be used for diagnosing and monitoring dermatitis (skin inflammation). Skin infection (or inflammation) is evidenced by itching, lesions, and redness. The inflammation can be induced by local skin irritants (acids, alkalies, corrosives, and poison ivy), hyper-susceptibility to environmental agents, or systemic disease. The diagnosis and monitoring of skin inflammation includes but is not limited to: actinic dermatitis, allergic dermatitis, atopic dermatitis, berlock dermatitis or berloque dermatitis, cercarial dermatitis, schistosome dermatitis, or swimmer's itch, contact dermatitis or dermatitis venenata, cosmetic dermatitis, dermatitis calorica, dermatitis herpetiformis, dermatitis hiemalis, dermatitis infectiosa eczematoides, dermatitis medicamentosa, dermatitis multiformis, dermatitis papillaris capillitti, dermatitis seborrheica, dermatitis venenata, dermatitis verrucosa, diaper dermatitis, exfoliative dermatitis, factitial dermatitis, photoallergic dermatitis, poison ivy dermatitis, primary dermatitis, radiation dermatitis, rhus dermatitis, schistosome dermatitis, stasis dermatitis, x-ray dermatitis, dermatitis seborrheica, dermatitis venenata, or dermatitis verrucosa.

Third, the present invention may be used for diagnosing and monitoring of allergic skin lesions. An allergy is due to an acquired and abnormal immune response to a substance (allergen). Allergies can produce a broad range of inflammatory responses on the skin such as itching, rashes, or lesions.

Fourth, the present invention may be used for diagnosing and monitoring allergic skin tests. Skin tests are used to diagnose or monitor suspected allergens, pathogens, or sensitizers applied to the skin. A variety of tests have been developed to detect an individual's sensitivity to specific allergens or pathogens. The present invention can be used for rapid and early diagnosis and monitoring of skin tests including, but not limited to: Allergen testing (intradermal test, prick test, puncture test, scratch test) tuberculin testing, mantoux testing, or PPD (purified protein derivative testing).

Although the best mode contemplated by the inventors of carrying out the present invention is disclosed above, practice of the present invention is not limited thereto. It will be manifest that various additions, modifications and rearrangements of the features of the present invention may be made without deviating from the spirit and scope of the underlying inventive concept.

Moreover, the individual components need not be formed in the disclosed shapes, or assembled in the disclosed configuration, but could be provided in virtually any shape, and assembled in virtually any configuration, which operate together so as to provide objective tissue injury analysis. Further, although the tissue injury analysis equipment described herein is a physically separate module, it will be manifest that the equipment may be integrated into the apparatus with which it is associated. Furthermore, all the disclosed features of each disclosed embodiment can be combined with, or substituted for, the disclosed features of every other disclosed embodiment except where such features are mutually exclusive.

It is intended that the appended claims cover all such additions, modifications and rearrangements. Expedient embodiments of the present invention are differentiated by the appended subclaims.

We claim:

1. A method of assessing an injury to tissue comprising:
   (A) reflecting an electromagnetic signal from said tissue to produce a reflected electromagnetic signal;
   (B) producing spectral data pertaining to the intensities of individual wavelengths of said reflected electromagnetic signal;
   (C) compressing said spectral data to produce compressed spectral data; said compressing step being performed before a processing step such that, during said processing step, compressed spectral data is processed;
   (D) analyzing said spectral data to obtain a set of results; and
   (E) providing an indication of the nature of said injury to said tissue based upon said set of results.

2. The method according to claim 1, wherein said analyzing step is performed using a system of equations having the form:

$$\left\{ \begin{array}{l} y_1 = f_1^2\left[\sum_j c_{j1}^2 f_1^1\left[\sum_i c_{ij}^1 s_i\right]\right] \\ \vdots \\ y_k = f_k^2\left[\sum_j c_{jk}^2 f_k^1\left[\sum_i c_{ij}^1 s_i\right]\right] \end{array} \right\}$$

where the functions $f_k^n$ are single-valued functions, $c_{ij}^n$ and $c_{jk}^n$ are coefficients from a matrix, and $y_1 \ldots y_k$ are the outputs of analyzing step and are proportional to the probability that the tissue injury is of class k.

3. The method according to claim 2, wherein said coefficients are fixed.

4. A method of assessing an injury to tissue comprising:
   (A) generating a first electromagnetic signal; then
   (B) reflecting said first electromagnetic signal from said tissue to produce a second electromagnetic signal; then
   (C) transmitting said second electromagnetic signal to a spectrometer; then
   (D) producing spectral data pertaining to said second electromagnetic signal using said spectrometer, said spectral data including information pertaining to the intensities of individual wavelengths of said second electromagnetic signal; then
   (E) compressing said spectral data to produce compressed spectral data; said compressing step being performed before a processing step such that, during said processing step, compressed spectral data is processed;
   (F) analyzing said spectral data to obtain a set of results, said set of results indicating the nature of said injury to said tissue; and
   (G) providing an indication of the nature of said injury to said tissue based upon said set of results.

5. The method according to claim 4, wherein said analyzing step is performed using a system of equations having the form:

$$\left\{ \begin{array}{l} y_1 = f_1^2\left[\sum_j c_{j1}^2 f_1^1\left[\sum_i c_{ij}^1 s_i\right]\right] \\ \vdots \\ y_k = f_k^2\left[\sum_j c_{jk}^2 f_k^1\left[\sum_i c_{ij}^1 s_i\right]\right] \end{array} \right\}$$

where the functions $f_k^n$ are single-valued functions, $c_{ij}^n$ and $c_{jk}^n$ are coefficients from a matrix, and $y_1 \ldots y_k$ are the outputs of said analysis step and are proportional to the probability that the tissue injury is of class k.

6. The method according to claim 4, further comprising compressing said spectral data to produce compressed spectral data, said compressing step including transforming said spectral data to a representation in which said spectral data is represented using a plurality of coefficients, the total number of said coefficients being relatively small as compared to the total number of wavelengths for which intensity information is produced during the producing step (D), each of said coefficients corresponding to one of a plurality of orthogonal eigen-spectra of the transformation, and said compressing step being performed before said processing step.

7. An apparatus for assessing an injury to a tissue, comprising:
   an electromagnetic signal generator;
   an optical fiber connected to said electromagnetic signal generator;
   a fiber optic probe connected to said optical fiber;
   a broad band spectrometer connected to said fiber optic probe; and
   a computer connected to said broad band spectrometer, said computer analyzing data from said broad band spectrometer to produce a plurality of outputs, each of said plurality of outputs corresponding to a tissue injury category; and
   wherein said computer includes a principle component analyzer of broad band spectral data obtained from said broad band spectrometer; and wherein said computer produces a set of results at said plurality of outputs, said set of results indicating the nature of said injury to said tissue.

8. The apparatus according to claim 7, wherein the result at each of said plurality of outputs indicates the probability that said injury to said tissue is in said tissue injury category that corresponds to the respective output.

9. The apparatus according to claim 7, wherein said computer includes:

an autoscaling processor;

a singular value decomposition analyzer coupled to said autoscaling processor; and a classifier coupled to said singular value decomposition analyzer.

10. The apparatus according to claim 7, further comprising a sample enclosure.

11. The apparatus according to claim 7, further comprising a positioner operatively connected to said fiber optic probe.

12. The apparatus according to claim 7, wherein one of said plurality of outputs corresponds to a full thickness burn injury and another of said plurality of outputs corresponds to a partial thickness burn injury.

13. A method of assessing an injury to tissue, the method comprising:

reflecting an electromagnetic signal off said tissue to produce a reflected electromagnetic signal;

measuring the intensities of individual wavelengths of said reflected electromagnetic signal to produce spectrum data;

compressing said spectrum data and extracting features from said spectrum data, including the step of extracting a set of orthogonal feature vectors to represent said spectrum data; and classifying said set of orthogonal feature vectors, including the step of producing a set of results at a plurality of outputs, each of said outputs corresponding to a tissue injury category, and said set of results indicating the nature of said injury to said tissue.

14. The method according to claim 13, wherein a first one of said plurality of outputs corresponds to a full thickness burn injury and a second one of said plurality of outputs corresponds to a partial thickness burn injury.

15. The method according to claim 14, wherein the result at said first one of said plurality of outputs indicates the probability that said tissue injury is a full thickness burn injury and wherein the result at said second one of said plurality of outputs indicates the probability that said tissue injury is a partial thickness burn injury.

* * * * *